(12) United States Patent
Wilk et al.

(10) Patent No.: US 6,254,564 B1
(45) Date of Patent: Jul. 3, 2001

(54) LEFT VENTRICULAR CONDUIT WITH BLOOD VESSEL GRAFT

(75) Inventors: Peter J. Wilk, New York, NY (US); David Y. Phelps, Louisville, KY (US); Scott J. Wolf, Minneapolis, MN (US)

(73) Assignee: Percardia, Inc., Nashua, NH (US)

( * ) Notice: Subject to any disclaimer, the term of this patent is extended or adjusted under 35 U.S.C. 154(b) by 0 days.

(21) Appl. No.: 09/369,061

(22) Filed: Aug. 4, 1999

Related U.S. Application Data
(60) Provisional application No. 60/099,719, filed on Sep. 10, 1998.

(51) Int. Cl.[7] .......................... A61M 5/00; A61M 25/00; A61F 2/06; A61F 2/04

(52) U.S. Cl. .................... 604/9; 604/8; 604/264; 623/1.24; 623/1.1; 623/12

(58) Field of Search ............ 604/8–10, 246–47, 604/264; 623/1, 11, 12, 1.1, 1.13, 1.14, 1.24; 606/108, 191–200, 153

(56) References Cited

U.S. PATENT DOCUMENTS

| | | | |
|---|---|---|---|
| 4,441,215 | * | 4/1984 | Kaster ........................ 3/1.4 |
| 4,546,499 | | 10/1985 | Possis et al. . |
| 4,562,597 | | 1/1986 | Possis et al. . |
| 4,733,665 | | 3/1988 | Palmaz . |

(List continued on next page.)

FOREIGN PATENT DOCUMENTS

| | | |
|---|---|---|
| 0 876 803 | 11/1998 | (EP) . |
| 97/13463 | 4/1997 | (WO) . |
| 97/13471 | 4/1997 | (WO) . |
| 97/27893 | 8/1997 | (WO) . |

(List continued on next page.)

OTHER PUBLICATIONS

Gardner, M.D. et al., "An Experimental Anatomic Study of Indirect Myocardial Revascularization," *Journal of Surgical Research*, May 1971, vol. 11, No. 5, pp. 243–247.

Palmaz et al., "Expandable Intrahepatic Protacaval Shunt Stents: Early Experience in the Dog," *AJR*, 1985, vol. 145, pp. 821–825.

Palmaz et al., "Expandable Intrahepatic Protacaval Shung Stents in Dogs with Chronic Portal Hypertension," *AJR*, 1986, vol. 147, pp. 1251–1254.

Richter, M.D. et al., "Transjugular Intrahepatic Protacaval Stent Shunt: Preliminary Clinical Results," *Radiology*, 1990, vol. 174, No. 3, pp. 1027–1030.

Zemel, M.D. et al., "Percutaneous Transjugular Portosystemic Shunt," *JAMA*, 1991, vol. 266, No. 3, pp. 390–393.

Massimo, M.D. et al., "Myocardial Revascularization by a New Method of Carrying Blood Directly from the Left Ventricular Cavity into the Coronary Circulation," *Journal of Thoracic Surgeons*, Aug. 1997, vol. 34, No. 2, pp. 257–264.

Lary, M.D. et al., "Myocardial Revascularization Experiments Using the Epicardium," *Archives of Surgery*, Jan. 1969, vol. 98, No. 1, pp. 69–72.

(List continued on next page.)

*Primary Examiner*—Angela D. Sykes
*Assistant Examiner*—Patricia M Bianco
(74) *Attorney, Agent, or Firm*—Finnegan, Henderson, Farabow, Garrett & Dunner, L.L.P.

(57) ABSTRACT

Disclosed is a conduit that provides a bypass around an occlusion or stenosis in a coronary artery. The conduit is a tube adapted to be positioned in the heart wall to provide a passage for blood to flow between a heart chamber and a coronary artery, at a site distal to the occlusion or stenosis. The conduit has a section of blood vessel attached to its interior lumen which preferably includes at least one naturally occurring one-way valve positioned therein. The valve prevents the backflow of blood from the coronary artery into the heart chamber.

38 Claims, 2 Drawing Sheets

U.S. PATENT DOCUMENTS

| | | |
|---|---|---|
| 4,769,029 | 9/1988 | Patel . |
| 5,147,388 | 9/1992 | Yamazaki . |
| 5,258,008 | 11/1993 | Wilk . |
| 5,275,580 | 1/1994 | Yamazaki . |
| 5,287,861 | 2/1994 | Wilk . |
| 5,330,486 | 7/1994 | Wilk . |
| 5,409,019 | 4/1995 | Wilk . |
| 5,429,144 * | 7/1995 | Wilk ................................... 128/898 |
| 5,456,712 | 10/1995 | Maginot . |
| 5,470,320 | 11/1995 | Tifenbrun et al. . |
| 5,500,014 | 3/1996 | Quijano et al. . |
| 5,527,337 | 6/1996 | Stack et al. . |
| 5,571,167 | 11/1996 | Maginot . |
| 5,609,626 | 3/1997 | Quijano et al. . |
| 5,655,548 | 8/1997 | Nelson et al. . |
| 5,662,124 | 9/1997 | Wilk . |
| 5,755,682 | 5/1998 | Knudson . |
| 5,758,663 | 6/1998 | Wilk et al. . |
| 5,797,946 | 8/1998 | Chin . |
| 5,810,836 | 9/1998 | Hussein et al. . |
| 5,824,038 | 10/1998 | Wall . |
| 5,824,071 | 10/1998 | Nelson et al. . |
| 5,830,222 | 11/1998 | Makower . |
| 5,865,723 | 2/1999 | Love . |
| 5,878,751 | 3/1999 | Hussein et al. . |
| 5,908,028 | 1/1999 | Wilk . |
| 5,908,029 | 6/1999 | Knudson et al. . |
| 5,935,119 | 8/1999 | Guy et al. . |
| 5,944,019 | 8/1999 | Knudson et al. . |
| 5,971,993 | 10/1999 | Hussein et al. . |
| 5,976,178 | 11/1999 | Goldstein et al. . |
| 5,976,192 | 11/1999 | McIntyre et al. . |
| 5,976,650 | 11/1999 | Campbell et al. . |
| 5,979,455 | 11/1999 | Maginot . |
| 5,980,548 | 11/1999 | Evans et al. . |
| 5,984,956 | 11/1999 | Tweden et al. . |
| 5,989,276 | 11/1999 | Houser et al. . |
| 5,989,287 | 11/1999 | Yang et al. . |
| 5,993,481 | 11/1999 | Marcade et al. . |
| 5,997,573 | 12/1999 | Quijano et al. . |
| 6,001,123 | 12/1999 | Lau . |
| 6,004,261 | 12/1999 | Sinofsky et al. . |
| 6,029,672 | 2/2000 | Vanney et al. . |
| 6,033,582 * | 3/2000 | Lee et al. ................................ 216/37 |
| 6,042,581 | 3/2000 | Ryan et al. . |
| 6,045,565 | 4/2000 | Ellis et al. . |
| 6,053,924 | 4/2000 | Hussein . |
| 6,053,942 | 4/2000 | Eno et al. . |
| 6,068,638 | 5/2000 | Makower . |
| 6,071,292 | 6/2000 | Makower et al. . |
| 6,076,529 | 6/2000 | Vanney et al. . |
| 6,080,163 | 6/2000 | Hussein et al. . |
| 6,092,526 | 7/2000 | Lafontaine et al. . |
| 6,093,166 | 7/2000 | Knudson et al. . |

FOREIGN PATENT DOCUMENTS

| | | |
|---|---|---|
| 97/27898 | 8/1997 | (WO) . |
| 97/32551 | 9/1997 | (WO) . |
| 98/08456 | 3/1998 | (WO) . |
| 98/10714 | 3/1998 | (WO) . |
| 98/16161 | 4/1998 | (WO) . |
| 98/46115 | 10/1998 | (WO) . |
| 98/46119 | 10/1998 | (WO) . |
| 98/53759 | 12/1998 | (WO) . |
| 98/55027 | 12/1998 | (WO) . |
| 98/57591 | 12/1998 | (WO) . |
| 99/08624 | 2/1999 | (WO) . |
| 99/49793 | 3/1999 | (WO) . |
| 99/21510 | 5/1999 | (WO) . |
| 99/22656 | 5/1999 | (WO) . |
| 99/36000 | 7/1999 | (WO) . |
| 99/36001 | 7/1999 | (WO) . |
| 99/38459 | 8/1999 | (WO) . |
| 99/40868 | 8/1999 | (WO) . |
| 99/47071 | 9/1999 | (WO) . |
| 99/48545 | 9/1999 | (WO) . |
| 99/49910 | 10/1999 | (WO) . |
| 99/51162 | 10/1999 | (WO) . |
| 99/53863 | 10/1999 | (WO) . |
| 99/60941 | 12/1999 | (WO) . |
| 99/62430 | 12/1999 | (WO) . |
| 00/09195 | 2/2000 | (WO) . |
| 00/10623 | 3/2000 | (WO) . |
| 00/12029 | 3/2000 | (WO) . |
| 00/15146 | 3/2000 | (WO) . |
| 00/15147 | 3/2000 | (WO) . |
| 00/15148 | 3/2000 | (WO) . |
| 00/15149 | 3/2000 | (WO) . |
| 0015275 | 3/2000 | (WO) . |
| 00/21436 | 4/2000 | (WO) . |
| 00/21461 | 4/2000 | (WO) . |
| 00/21463 | 4/2000 | (WO) . |
| 00/24449 | 5/2000 | (WO) . |

OTHER PUBLICATIONS

Munro, M.D. et al., "The possibility of myocardial revascularization by creation of a left ventriculcoronary artery fistula," *Journal of Thoracic and Cardiovascular Surgery*, Jul. 1969, vol. 58, No. 1, pp. 25–32.

Kuzela, M.D. et al., "Experimental evaluation fo direct transventricular revascularization," *The Journal of Thoracic and Cardiovascular Surgery*, Jun. 1969, vol. 57, No. 6, pp. 770–773.

Levinsky, L. et al., "The Revival of the Horseshoe Graft," *Thorac.cardiovasc. Surgeon*, 27, pp. 322–324, 1979.

Mills, Noel L. et al., "Valvulotomy of valves in the saphenous vein graft before coronary artery bypass," *The Journal of Thoracic and Cardiovascular Surgery*, 71(6), pp. 878–879, Jun. 1976.

Baba et al., "Hemodynamic effects of venous valves in aorto–coronary bypass grafts," *The Journal of Thoracic and Cardiovascular Surgery*, 71(5), pp. 774–778, May 1976.

Phillips, Steven J. M.D. et al, "Improvement in Forward Coronary Blood Flow by Using a Reversed Saphenous Vein with a Competent Valve," *The Annals of Thoracic Surgery*, 21(1), pp. 12–15, Jan. 1976.

Tweden et al., "Ventriculocoronary Artery Bypass (VCAB), a Novel Approach to Myocardial Revascularization," #2000–4653, Feb. 2000.

* cited by examiner

US 6,254,564 B1

LEFT VENTRICULAR CONDUIT WITH BLOOD VESSEL GRAFT

CROSS-REFERENCE TO RELATED APPLICATION

This application claims the benefit of U.S. Provisional Application Serial No. 60/099,719, filed Sep. 10, 1998.

Field of the Invention

This invention relates to apparatus and method for implanting a conduit to allow communication of fluids from one portion of a patient's body to another; and, more particularly, to a blood flow conduit to allow communication from a heart chamber to a vessel or vice versa, and/or vessel to vessel. Even more particularly, the invention relates to a left ventricular conduit and related conduit configurations having a blood vessel graft incorporated therein for controlling the flow of blood through the conduit to achieve bypass of an occluded or stenosed coronary artery.

Background of the Invention

Coronary artery disease is a major problem in the U.S. and throughout the world. Coronary arteries as well as other blood vessels frequently become clogged with plaque which, at the very least, can reduce blood and oxygen flow to the heart muscle (myocardium), and may impair the efficiency of the heart's pumping action, and can lead to heart attack (myocardial infarction) and death. In some cases, these coronary arteries can be unblocked through noninvasive techniques such as balloon angioplasty. In more difficult cases, a surgical bypass of the blocked vessel is necessary.

In a coronary bypass operation, one or more venous segments are inserted between the aorta and the coronary artery, or, alternatively, the distal end of an internal mammary artery is anastomosed to the coronary artery at a site distal to the stenosis or occlusion. The inserted venous segments or transplants act as a bypass of the blocked portion of the coronary artery and thus provide for a free or unobstructed flow of blood to the heart. More than 500,000 bypass procedures are performed in the U.S. every year.

Such coronary artery bypass graft (CABG) surgery, however, is a very intrusive procedure which is expensive, time-consuming, and traumatic to the patient. The operation requires an incision through the patient's sternum (sternotomy), and that the patient be placed on a heart-lung bypass pump so that the heart can be operated on while not beating. A saphenous vein graft is harvested from the patient's leg, another highly invasive procedure, and a delicate surgical procedure is required to piece the bypass graft to the coronary artery (anastomosis). Hospital stays subsequent to the surgery and convalescence are prolonged. Furthermore, many patients are poor surgical candidates due to other concomitant illnesses.

As mentioned above, another conventional treatment is percutaneous transluminal coronary angioplasty (PTCA) or other types of angioplasty. However, such vascular treatments are not always indicated due to the type or location of the blockage or stenosis, or due to the risk of emboli.

Thus, there is a need for an improved coronary bypass system which is less traumatic to the patient.

SUMMARY OF THE INVENTION

The present invention addresses the need in the previous technology by providing a coronary bypass system which avoids a sternotomy and other intrusive aspects associated with coronary bypass surgery. It also frees the surgeon from having to perform multiple anastomoses, as is necessary in the current process.

The present device provides a conduit for diverting blood directly from a heart chamber, such as the left ventricle of the heart, to the coronary artery distal to the blockage or stenosis, thereby bypassing the blocked portion of the vessel. The conduit comprises a tube adapted to be positioned in the heart wall and having a section of blood vessel attached to the interior of the conduit, to provide a passage for blood flow which is similar to the body's own blood vessels.

The conduit device is delivered through the coronary artery to a position distal the blockage or stenosis. At that position, the coronary artery and the wall of the left ventricle, including the myocardium, are pierced to provide an opening or channel completely through from the coronary artery to the left ventricle of the heart. The conduit is then positioned in the opening to provide a permanent passage for blood to flow between the left ventricle of the heart and the coronary artery, distal to the blockage or stenosis.

The conduit is sized so that one open end is positioned within the coronary artery, while the other open end is positioned in the left ventricle. Prior to implantation of the conduit, a section of vein or other blood vessel is obtained from the patient, from another human donor, or from a nonhuman animal. The vein or other blood vessel is sized so as to fit within the interior of the conduit. The hollow lumen of the conduit with the blood vessel graft inserted therein provides a passage for the flow of blood.

If desired, the section of blood vessel inserted into the conduit may include one or more naturally occurring one-way valves. The valve prevents the backflow of blood from the myocardium into the left ventricle. For example, a section of vein having a valve therein can be used. Alternatively, the pulmonic valve or aortic valve obtained from a nonhuman animal, such as a fetal pig or piglet, can be used to provide a one-way passage for the flow of blood through the conduit.

DETAILED DESCRIPTION OF THE PREFERRED-EMBODIMENT

Figure 1A:
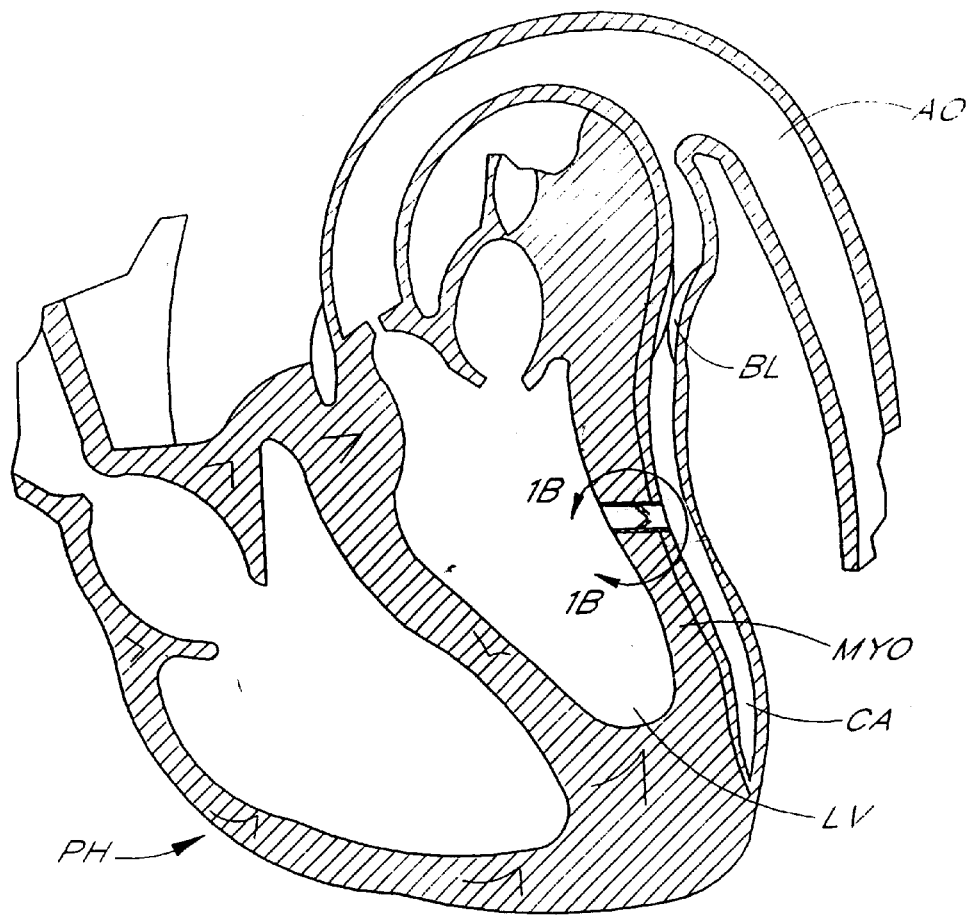
FIG. 1A is a schematic, cross-sectional view of a human heart, showing a conduit in the myocardium of the heart for forming a bypass between the left ventricle and a coronary artery.

As is well known, the coronary artery branches off the aorta and is positioned along the external surface of the heart wall. Oxygenated blood that has returned from the lungs to the heart then flows from the heart to the aorta. Some blood in the aorta flows into the coronary arteries, and the remainder of blood in the aorta flows on to the rest of the body. The coronary arteries are the primary blood supply to the heart muscle and are thus critical to life. In some individuals, atherosclerotic plaque, aggregated platelets, and/or thrombi build up within the coronary artery, blocking the free flow of blood and causing complications ranging from mild angina to heart attack and death. The presence of coronary vasospasm, also known as "variant angina" or "Prinzmetal's angina," compounds this problem in many patients.

As used herein, the term "heart chamber" primarily refers to the interior, or lumenal, aspect of the left or right ventricle or the left or right atrium. The term "conduit," "stent," and "tube" herein refer to physical structures, preferably primarily artificial, that can be positioned between two or more chambers or vessels, to allow blood flow from one chamber or vessel to another. A "shunt" is any natural or artificial passage between natural channels, such as heart chambers or blood vessels. The conduit in the preferred arrangement can be made of a variety of materials, including various metals, such as nitinol, or plastics.

As used herein, the term "heart wall" comprises any one or more of the following portions or layers of the mammalian heart: the epicardium, myocardium, endocardium, pericardium, interatrial septum, and interventricular septum.

The principles of the present invention are not limited to left ventricular conduits, and include conduits for communicating bodily fluids from any space within a patient to another space within a patient, including any mammal. Furthermore, such fluid communication through the conduits is not limited to any particular direction of flow and can be antegrade or retrograde with respect to the normal flow of fluid. Moreover, the conduits may communicate between a bodily space and a vessel or from one vessel to another vessel (such as an artery to a vein or vice versa). Moreover, the conduits can reside in a single bodily space so as to communicate fluids from one portion of the space to another. For example, the conduits can be used to achieve a bypass within a single vessel, such as communicating blood from a proximal portion of an occluded coronary artery to a more distal portion of that same coronary artery.

In addition, the conduits and related methods can preferably traverse various intermediate destinations and are not limited to any particular flow sequence. For example, in one preferred embodiment of the present invention, the conduit communicates from the left ventricle, through the myocardium, into the pericardial space, and then into the coronary artery. However, other preferred embodiments are disclosed, including direct transmyocardial communication from a left ventricle, through the myocardium and into the coronary artery. Thus, as emphasized above, the term "transmyocardial" should not be narrowly construed in connection with the preferred fluid communication conduits, and other nonmyocardial and even noncardiac fluid communication are preferred as well. With respect to the walls of the heart (and more specifically the term "heart wall"), the preferred conduits and related methods are capable of fluid communication through all such walls including, without limitation, the pericardium, epicardium, myocardium, endocardium, septum, etc.

The bypass which is achieved with certain preferred embodiments and related methods is not limited to a complete bypass of bodily fluid flow, but can also include a partial bypass which advantageously supplements the normal bodily blood flow. Moreover, the obstructions that are bypassed may be of a partial or complete nature, and therefore the terminology "bypass" or "occlusion" should not be construed to be limited to a complete bypass or a complete occlusion but can include partial bypass and partial occlusion as described.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Moreover, the conduits are not necessarily stented or lined with a device but can comprise mere tunnels or openings formed in the tissues of the patient.

The conduits of the present invention preferably comprise both integral or onepiece conduits as well as plural sections joined together to form a continuous conduit. The present conduits can be deployed in a variety of methods consistent with sound medical practice including vascular or surgical deliveries, including minimally invasive techniques. For example, various preferred embodiments of delivery rods and associated methods are disclosed. In one embodiment, the delivery rod is solid and trocar-like. It may be rigid or semi-rigid and capable of penetrating the tissues of the patient and thereby form the conduit, in whole or in part, for purposes of fluid communication. In other preferred embodiments, the delivery rods may be hollow so as to form the conduits themselves (e.g., the conduits are preferably self-implanting or self-inserting) or have a conduit mounted thereon (e.g., the delivery rod is preferably withdrawn leaving the conduit installed). Thus, the preferred conduit device and method for installation is preferably determined by appropriate patient indications in accordance with sound medical practices.

In order to restore the flow of oxygenated blood through the coronary artery, the preferred arrangement provides for the shunting of blood directly from the heart to a site in the coronary artery which is distal the blockage or stenosis.

Although the specification herein will describe the conduit primarily with reference to the left ventricle, the preferred arrangement can be used with any of the four heart chambers, and with any coronary artery, including the left main coronary artery, the right coronary artery, the left anterior descending artery, the left circumflex artery, the posterior descending artery, the obtuse marginal branch or a diagonal branch.

A tunnel or opening is formed through the wall of the coronary artery and the myocardium and into the left ventricle of the heart which lies beneath, or deep to, the coronary artery. A conduit is positioned in the opening to keep it open.

The conduit may be introduced into the myocardium in a variety of ways, including by a catheter threaded through the femoral artery into the aorta and thence into the left ventricle and, if necessary, the left atrium; or by a catheter threaded through the femoral vein into the inferior vena cava and thence into the right atrium and right ventricle. Alternatively, the conduit may be introduced through a surgical incision in chest wall (thoracotomy) or sternum (sternotomy).

Further details regarding conduits and conduit delivery systems are described in copending patent applications entitled DELIVERY METHODS FOR LEFT VENTRICULAR CONDUIT, having U.S. patent application Ser. No. 09/368,868, DESIGNS FOR LEFT VENTRICULAR CONDUIT, having U.S. patent application Ser. No. 09/369,011, VALVE DESIGNS FOR LEFT VENTRICULAR CONDUIT, having U.S. patent application Ser. No. 09/368,393, LEFT VENTRICULAR CONDUITS TO CORONARY ARTERIES AND METHODS FOR CORONARY BYPASS, and BLOOD FLOW CONDUIT DELIVERY SYSTEM AND METHOD OF USE, U.S. Ser. No. 09/638,644, filed on the same day as the present application, and U.S. Pat. Nos. 5,429,144 and 5,662,124, the disclosures of which are all hereby incorporated by reference in their entirety.

The opening through the heart wall (including endocardium, myocardium, and epicardium) and coronary artery can be formed in a variety of ways, including by knife or scalpel, electrocautery, cryoablation, radiofrequency ablation, ultrasonic ablation, and the like. Other methods will be apparent to those of ordinary skill in the art.

The conduit is provided with a section of vein or other blood vessel positioned within its interior lumen. The section of vein or other blood vessel is obtained from the patient, from a donor, or from an animal. Prior to implantation of the conduit, a segment of blood vessel sized to fit with the lumen of the conduit is inserted into the conduit. The conduit with the graft therein provides a passage for the flow of blood which is similar to the natural human blood vessels. The segment of vein or other blood vessel harvested to fit within the conduit may include one or more of the valves which naturally occur in the human body. These valves act to prevent the backflow of blood. In the conduit, these naturally occurring venous valves prevent the blood from flowing back into the left ventricle of the heart from the coronary artery. The segment of vein is preferably inserted into the conduit prior to the conduit's deployment into the human body by any of various surgical or catheter-guided techniques known to those of skill in the art.

Figure 1B:
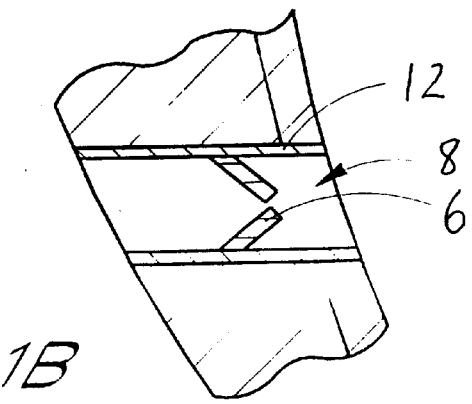
FIG. 1B is an enlarged view of the bypass conduit of FIG. 1A.

Referring now to FIGS. 1A and 1B, a coronary artery bypass is accomplished by disposing a conduit 12 (FIG. 1B) in a heart wall or myocardium MYO of a patient's heart PH (FIG. 1A). The conduit 12 preferably extends from the left ventricle LV of heart PH to a clogged coronary artery CA at a point downstream of a blockage BL to create a passageway 8 therethrough. Conduit 12 is preferably made of a biocompatible material such as stainless steel or nitinol, although other materials such as Ti, Ti alloys, Ni alloys, Co alloys and biocompatible polymers may also be used. In one embodiment, conduit 12 has a one way valve 6 to allow blood to flow from the left ventricle LV to the coronary artery CA. Although the conduit 12 may elastically deform under the contractive pressure of the heart muscle during systole, the stent remains open to allow blood to pass from the patient's left ventricle LV into the coronary artery CA. During diastole, the blood pumped into coronary artery through passageway 8 is blocked by one-way valve 6 from returning to left ventricle LV.

Figure 2:
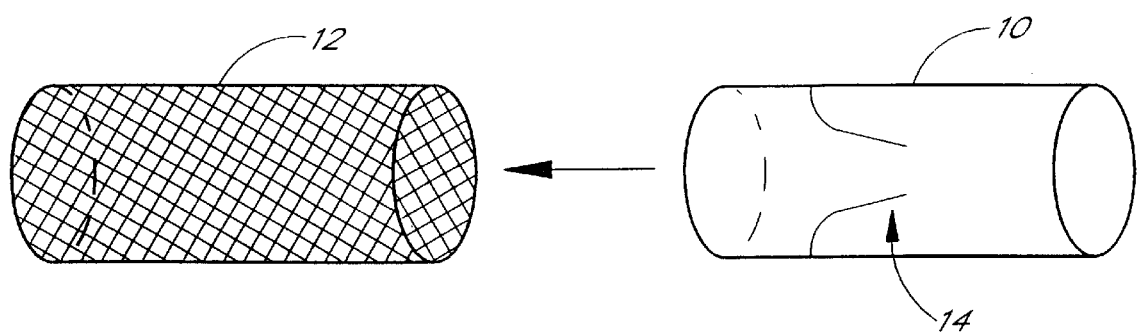
FIG. 2 is an exploded view of a vein graft incorporated into a heart conduit in accordance with the preferred arrangement.

As shown in FIG. 2, a preferred embodiment involves the use of a vein graft 10 taken from the patient. Prior to preparing the conduit 12 for placement in the patient, a section of vein 10 is obtained from the patient (i.e., an autologous graft or autograft). Of course, a blood vessel taken from another human donor (i.e., an allogeneic graft or allograft) or nonhuman animal species (i.e., a heterologous graft or xenograft) could also be used. The vein 10 is preferably taken from the saphenous vein in the leg of the patient. Alternatively, a donor vein could be used, or a fetal pig or piglet can be obtained and dissected to remove a section of the pulmonary artery having a pulmonic valve therein, or a section of the aorta having an aortic valve therein, or a similar vessel having a naturally occurring valve system. In other embodiments, the endothelial lining of a vein and/or a valve may be grown from one or more tissue cultures, utilizing cloning of donor cell lines or other genetic engineering techniques (or "tissue engineering") known to those of skill in the art. Thus, as used herein, "a section of blood vessel" may include one or more of the following: a surgically resected segment of a blood vessel, with or without one or more valves; the endothelial lining of a blood vessel, taken from an in vitro or in vivo specimen; and one or more venous valves, taken from in vitro or in vivo specimens.

As noted above, the section of vein 10 or other blood vessel harvested preferably contains one or more valves 14, which occur naturally in the veins. The section of vein 10 may also not have a valve. The vein section 10 is sized so as to be the same length as the conduit 12. The vein section 10 is placed within the interior lumen of the conduit 12 and attached to the inside of the conduit 12 by suturing or other attachment methods. The natural vein graft 10 is biocompatible and therefore reduces problems associated with rejection of the conduit 12 and clotting around or in the conduit 12. In addition, the vein 10 provides a natural valve system 14 that is already used throughout the human body to prevent the backflow of blood. In the case of a xenograft, treatment of the graft with chemicals, such as glutaraldehyde, may be undertaken to remove living cells, including antigenic materials, from the connective tissue framework of the graft so as to reduce thrombogenicity and antigenicity.

Figure 3:
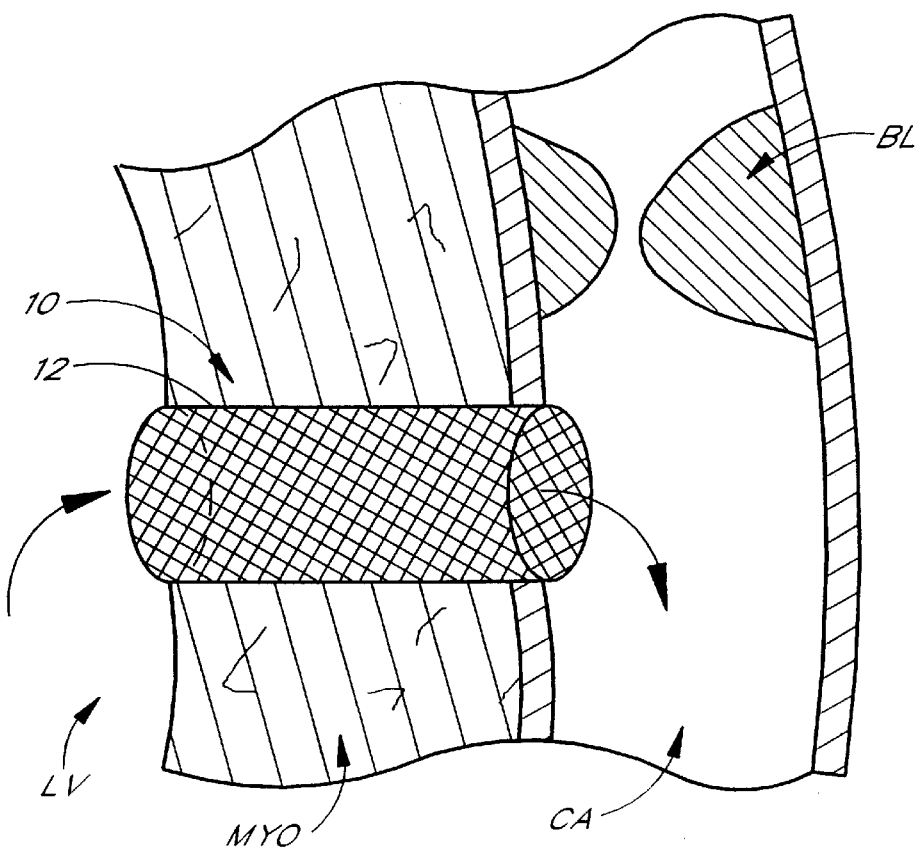
FIG. 3 is a close-up, cross-sectional view of a blockage or stenosis in the coronary artery, illustrating the conduit of the preferred arrangement positioned so as to bypass the blockage or stenosis.

Referring now to FIG. 3, a self-expanding conduit 12 having a section of vein 10 therein is introduced into the wall of the myocardium MYO as follows. A conduit delivery catheter (not shown), having the compressed conduit 12 mounted on its distal end, is advanced over a puncture mechanism and into the wall of the myocardium MYO at a site distal to the blockage or stenosis BL in the coronary artery CA. When the conduit 12 is properly seated in the myocardial wall MYO, its retaining sheath is withdrawn, allowing the conduit 12 to expand and open a passageway, or maintain patency of the passageway, from the left ventricle of the heart LV to the coronary artery CA. This allows oxygenated blood to flow directly from the left ventricle of the heart LV through the conduit 12 and to the coronary artery CA, bypassing the section of coronary artery CA that is blocked BL, as shown by the arrows in FIG. 3.

The conduit 12 may include attachment mechanisms not limited to hooks, barbs, large collars, and/or other methods to ensure that a seal is created between the coronary artery CA and the wall of the heart wall MYO, to prevent hemorrhaging and to prevent the threat of or actual conduit migration. When positioning and securing of the conduit 12 is completed, the remaining catheter assembly is removed, leaving the conduit 12 with the vein graft therein, in place in the body The present vascular conduit having a blood vessel graft incorporated therein provides significant improvements in the present treatment of blockages or stenoses in the coronary artery. Although the invention has been described in its preferred embodiments in connection with the particular figures, it is not intended that this description should be limited in any way by the foregoing.

What is claimed is:

1. A coronary bypass conduit comprising:
   a hollow tube having an interior and an exterior and configured to be positioned in a heart wall between a blood vessel and a heart chamber; and
   a section of body tissue positioned within said interior of said tube and adapted to allow blood to flow therethrough, wherein the section of body tissue contains at least one naturally occurring valve operable to restrict flow through the conduit from the blood vessel to the heart chamber during diastole.

2. The conduit of claim 1, wherein the section of body tissue is a section of a blood vessel.

3. The conduit of claim 2, wherein the blood vessel is a human vein.

4. The conduit of claim 2, wherein the section of blood vessel is an autograft.

5. The conduit of claim 2, wherein the section of blood vessel is an allograft.

6. The conduit of claim 2, wherein the section of blood vessel is a xenograft.

7. The conduit of claim 1, wherein said heart chamber is a left ventricle.

8. The conduit of claim 1, wherein said heart chamber is a right ventricle.

9. The conduit of claim 1, wherein said heart chamber is a left atrium.

10. The conduit of claim 1, wherein said heart chamber is a right atrium.

11. The conduit of claim 1, wherein said coronary artery is a left anterior descending artery.

12. The conduit of claim 1, wherein said coronary artery is a right coronary artery.

13. The conduit of claim 1, wherein said coronary artery is a circumflex coronary artery.

14. The conduit of claim 1, wherein said coronary artery is a posterior descending artery.

15. A bypass conduit for implantation in a body of a patient comprising:
    a hollow tube having an interior and an exterior; and
    a section of body tissue positioned within said interior of said tube and adapted to allow blood to flow therethrough, wherein the section of body tissue contains at least one naturally occurring valve operable to restrict flow through the conduit from the coronary artery to the heart chamber during diastole.

16. The method of claim 15, wherein the valve restricts flow through the conduit from the blood vessel to the left ventricle during diastole.

17. The conduit of claim 15, wherein the section of body tissue is a section of blood vessel.

18. A method of shunting blood from a first heart chamber or blood vessel to a second heart chamber or blood vessel, comprising:
    providing a conduit with two ends and an interior, and containing a section of body tissue positioned within the interior of said conduit, wherein the section of body tissue has at least one naturally occurring valve operable to restrict flow through the conduit from the second heart chamber or blood vessel to the first heart chamber or blood vessel during diastole; and
    placing said conduit such that one end of said conduit contacts said first heart chamber or blood vessel and the other end contacts said second heart chamber or blood vessel.

19. The method of claim 18, wherein said heart chamber is a left ventricle.

20. The method of claim 18, wherein said heart chamber is a right ventricle.

21. The method of claim 18, wherein said heart chamber is a left atrium.

22. The method of claim 18, wherein said heart chamber is a right atrium.

23. The method of claim 18, wherein said blood vessel is a left anterior descending artery.

24. The method of claim 18, wherein said blood vessel is a right coronary artery.

25. The method of claim 18, wherein said blood vessel is a left circumflex coronary artery.

26. The method of claim 18, wherein said blood vessel is a posterior descending artery.

27. The method of claim 18, wherein the section of body tissue is a section of blood vessel.

28. A method of shunting blood from a heart chamber to a coronary vessel, comprising:
    providing a conduit with two ends and containing a section of body tissue having at least one naturally occurring valve positioned within the interior of said conduit, wherein said naturally occurring valve is operable to restrict flow through the conduit from the coronary vessel to the heart chamber during diastole; and
    placing said conduit within a heart wall such that one end of said conduit is in flow communication with said heart chamber and the other end is in flow communication with said coronary vessel.

29. The method of claim 28, wherein the valve restricts flow through the conduit from the blood vessel to the left ventricle during diastole.

30. The method of claim 28, wherein the section of body tissue is a section of blood vessel.

31. A blood vessel bypass conduit comprising:
    a hollow tube having an interior and an exterior adapted to be positioned in a heart wall between a blood vessel and a heart chamber; and
    a section of body tissue positioned within said interior of said tube and adapted to allow blood to flow therethrough, wherein the section of body tissue contains a naturally occurring flow control mechanism to restrict blood flow through said tube and body tissue section from the blood vessel to the heart chamber during diastole.

32. The conduit of claim 31, wherein the section of body tissue is a section of blood vessel.

33. The conduit of claim 32, wherein said blood vessel comprises a vein.

34. The conduit of claim 32, wherein the section of blood vessel is an autograft.

35. The conduit of claim 32, wherein the section of blood vessel is an allograft.

36. The conduit of claim 32, wherein the section of blood vessel is a xenograft.

37. The conduit of claim 31, wherein the valve restricts flow through the tube and body tissue section from the blood vessel to the left ventricle during diastole.

38. The conduit of claim 31, wherein the flow control mechanism is configured to flow blood through the tube and body tissue section in predominantly one direction.

\* \* \* \* \*

UNITED STATES PATENT AND TRADEMARK OFFICE
CERTIFICATE OF CORRECTION

PATENT NO. : 6,254,564 B1
DATED : July 3, 2001
INVENTOR(S) : Peter J. Wilk et al.

It is certified that error appears in the above-identified patent and that said Letters Patent is hereby corrected as shown below:

<u>Title page,</u>
Item [54], in the Title, replace "LEFT VENTRICULAR CONDUIT WITH BLOOD VESSL GRAFT" with -- CONDUIT WITH VALVED BLOOD VESSEL GRAFT --;

<u>Column 6,</u>
Line 59, replace "blood vessel" with -- coronary artery --;
Line 64, replace "blood vessel" with -- coronary artery --;

<u>Column 7,</u>
Line 35, replace "blood vessel" with -- coronary artery --;

<u>Column 8,</u>
Line 27, replace "blood vessel" with -- coronary artery --;
Line 31, replace "blood vessel" with -- coronary artery --;
Line 33, replace "blood vessel" with -- coronary artery --;
Line 40, replace "blood vessel" with -- coronary artery --; and
Lines 53 and 54, replace "blood vessel" with -- coronary artery --.

Signed and Sealed this

Thirtieth Day of April, 2002

Attest:

Attesting Officer

JAMES E. ROGAN
*Director of the United States Patent and Trademark Office*